United States Patent [19]
Bisconte

[11] Patent Number: 5,976,892
[45] Date of Patent: Nov. 2, 1999

[54] METHOD AND APPARATUS FOR COUNTING CELLS AND MICROORGANISMS, PARTICULARLY IN FOOD AND BIOLOGICAL FLUIDS

[75] Inventor: Jean-Claude Bisconte, Briis-sous-Forges, France

[73] Assignee: Biocom, S.A., Les Ulis Cedex, France

[21] Appl. No.: 08/737,182

[22] PCT Filed: May 3, 1995

[86] PCT No.: PCT/FR95/00575

§ 371 Date: Jul. 25, 1997

§ 102(e) Date: Jul. 25, 1997

[87] PCT Pub. No.: WO95/30768

PCT Pub. Date: Nov. 16, 1995

[30] Foreign Application Priority Data

May 5, 1994 [FR] France ................................. 94 05551

[51] Int. Cl.⁶ .................................................. G01N 21/76
[52] U.S. Cl. ............................ 436/172; 436/63; 436/164; 436/177; 435/29; 435/34; 435/39; 435/808; 435/288.7; 422/82.05; 422/82.08; 422/101
[58] Field of Search ............................. 436/63, 164, 172, 436/177; 435/29, 34, 39, 808, 288.7; 422/82.05, 82.08, 101

[56] References Cited

U.S. PATENT DOCUMENTS

| | | | |
|---|---|---|---|
| 5,190,666 | 3/1993 | Bisconte | 210/744 |
| 5,306,420 | 4/1994 | Bisconte | 210/143 |
| 5,389,544 | 2/1995 | Sugata et al. | 435/39 |
| 5,403,720 | 4/1995 | Sato et al. | 435/31 |
| 5,428,441 | 6/1995 | Ogino et al. | 356/73 |
| 5,480,804 | 1/1996 | Niwa et al. | 435/286.1 |
| 5,627,042 | 5/1997 | Hirose et al. | 435/8 |

FOREIGN PATENT DOCUMENTS

| | | |
|---|---|---|
| 0148290 | 7/1985 | European Pat. Off. . |
| 0333560 | 9/1989 | European Pat. Off. . |
| 0397583 | 11/1990 | European Pat. Off. . |
| 0405480 | 1/1991 | European Pat. Off. . |
| 0443700 | 8/1991 | European Pat. Off. . |
| 0465987 | 1/1992 | European Pat. Off. . |
| 0529084 | 3/1993 | European Pat. Off. . |
| WO9003440 | 4/1990 | WIPO . |

OTHER PUBLICATIONS

Pettipher et al. *Letters in Applied Microbiology* vol. 14, pp. 206–209, 1992.

*Primary Examiner*—Maureen M. Wallenhorst
*Attorney, Agent, or Firm*—Weiser and Associates, P.C.

[57] ABSTRACT

A method for counting cells and microorganisms in a fluid medium, particularly in food and biological fluids, by labelling with a colored or fluorescent label which selectively labels the microorganisms and cells to be detected, and counting the labelled microorganisms and cells, wherein said colored or fluorescent label is a stoichiometric label, particularly a DNA or RNA label, the microorganisms and cells are concentrated at the same time as or prior to counting by means of a fluid medium concentration step, and counting is achieved by measuring the overall brightness of the concentrated medium and comparing it with a calibration curve.

19 Claims, 2 Drawing Sheets

METHOD AND APPARATUS FOR COUNTING CELLS AND MICROORGANISMS, PARTICULARLY IN FOOD AND BIOLOGICAL FLUIDS

BACKGROUND OF THE INVENTION

The present invention consists in a method and installation for counting cells and micro-organisms, in particular in food products or biological fluids.

SUMMARY OF THE INVENTION

There are various prior art methods of determining the presence of micro-organisms and cells, in particular cells, yeasts, mold, parasites or viruses in a food product, and of measuring the concentration of said micro-organisms and cells, for example for the purposes of quality control.

A first method entails culturing a sample of the product to be tested and, after a few days of incubation, observing the culture dish under a microscope in order to count the micro-organisms and cells.

This counting method necessitates a time-delay between taking the sample and obtaining the result, and is therefore not suited to real time testing. Moreover, this method leads to an assessment rather than to a precise count.

Another prior art proposal is to mark the micro-organisms and cells by means of chemical coloring agents in order to render them fluorescent, which makes the identification and counting of the micro-organisms and cells easier and introduces the possibility of automating the process by acquisition of a microscope image followed by signal processing on a computer. The effect of the signal processing is to recognize the marked micro-organisms and cells by discriminating them from the background and counting the number of objects recognized.

To speed up counting it has been proposed to combine this method of marking and automatic recognition of the marked objects with a filtration system increasing the concentration of the micro-organisms and cells to be counted.

European patent EP-A-0 333 560 describes a method of this kind in which the sample is first placed in contact with a fluorescent probe or antibody, after which the marked micro-organisms and cells are counted individually.

The system can also process cells such as polynuclear leukocytes in milk or human blood and urine. In this case the system is substituted for a flow cytometer.

The above prior art document suggests carrying out the count by microscope image analysis.

The applicant has developed an installation for automatic counting of marked cells and micro-organisms and cells sold under the tradename "COBRA" which counts micro-organisms and cells by scanning a plurality of focal planes of a membrane and carrying out image processing for each focal plane in order to recognize and to count the events looked for.

A device of this kind offers very high performance in the context of laboratory analysis and has made it possible to propose routine test approved by official bodies for testing food products in particular. Installations of this type are costly, however, since they utilize high-performance image acquisition means and sophisticated image processing systems. They are also unsuitable for use outside the laboratory, in the field, and are beyond the resources of smaller laboratories.

They also have two major drawbacks. Firstly, the prior art counting method is effected by sampling the total surface of the membrane, each image corresponding to a particular field of observation from several hundred or several thousand possible fields of observation. For the error rate of the count to be acceptable, the number of observation fields within which automatic counting is carried out must be increased, the number of fields to be analyzed being determined statistically and according to the time that can reasonably be allocated to carrying out an analysis. If the number of micro-organisms and cells, and therefore the density of events, is very low, the error rate becomes high. Moreover, the samples are no longer uniformly distributed and there are edge effects in particular.

Prior art systems have attempted to reduce the error rate by scanning the membrane in a manner that varies the position of the field of observation and the depth of the field of observation. This increases the number of image analysis sequences and therefore increases the overall analysis time.

The second drawback concerns situations in which the density of events is high, leading to the agglomeration of micro-organisms and cells. In these circumstances the automatic counting algorithms can treat an agglomeration of several hundred micro-organisms and cells as a single event, yielding a highly inaccurate result.

The trend in automatic equipment shows that the natural tendency of the person skilled in the art is continuously to improve the individual counting of events, from the visual counting of colonies formed by a culture on a nutrient medium in a PETRI dish through the association of filtration on a membrane and automatic counting by image processing to automating the displacement of the microscope in the X-Y directions and in the depth of field to multiply the number of fields analyzed. Another approach, also based on individual counting of events and known as flow cytometry, consists in counting individually events passing in a carrier flow.

The present invention goes fundamentally against this approach, which consists in improving techniques for counting individual events, in proposing an evaluation of the number of events by global acquisition of the luminescence of marked micro-organisms and cells fixed on a support.

The problem that the invention is directed to solving is that of increasing the reliability of the determination of the number of cells or micro-organisms, especially in the case of very low concentrations or very high concentrations.

The aim of the present invention is to propose a method of carrying out a rapid analysis of biological fluids using a simple and robust installation the acquisition cost of which is substantially lower than that of prior art devices and the operation of which is compatible with use in the field. In particular, it is desirable for the installation to be mobile in order to carry out fast testing of untreated milk at a production center, for the individual identification of the source of infection in the presence of somatic cells exceeding the allowed standard, and for immediate testing for the purposes of "quality payment" or health inspection of the producing animals.

To meet the above objectives, the invention is more particularly concerned with a method of counting cells and micro-organisms and cells present in a fluid medium, in particular food products or biological fluids, consisting in selectively marking with a colored or fluorescent marker the micro-organisms and cells to be detected and counting the micro-organisms and cells marked in this way, characterized in that the colored or fluorescent marker is a stoichiometric marker, for example a DNA marker or an RNA marker, in that, simultaneously with or prior to the counting, the micro-organisms and cells are concentrated by a step of filtering the fluid medium, the counting being effected by measurement of the global luminous intensity of the concentrated medium and by comparison of said luminous intensity with a calibration curve.

The method of the invention provides sufficient accuracy and enhanced reproducibility for most routine tests involving determination of the cellular concentration in a biological fluid, without using complex image processing techniques and providing a result whose reliability is not degraded by very low or very high concentrations, unlike the prior art individual counting methods.

In particular, for testing milk, the method of the invention is able to determine concentrations between 50,000 and 1,000,000 cells per millimeter of milk within a time period in the order of one second and for any number of samples from 1 to 24, simultaneously.

In a first embodiment, the marker is a coloring agent selectively marking the micro-organisms and cells to be detected and the counting is effected by measuring the global luminous intensity of the illuminated medium and by comparing said luminous intensity with a calibration curve. The measurement is effected by global measurement of the optical density of the marked events.

In a second embodiment, the marker is a fluorescent marker selectively marking the micro-organisms and cells to be detected constituted by a fluorescent probe and the counting is effected by measuring the global luminous intensity of the concentrated medium in the band of re-emission wavelengths of at least one of the fluorescent markers and by comparing said luminous intensity with a calibration curve.

Concentration can be effected in various ways, by the use of magnetic spherules carrying specific antibodies, by fixing on a microporous or other surface carrying grafted antibodies, or preferably by filtering with a microporous membrane.

In a preferred embodiment, the counting method includes a step of concentrating the micro-organisms and cells by a filtration step using a microporous membrane that is transparent at the excitation wavelengths of the fluorescent markers and the surface of which is normalized, the counting being effected by measuring the global luminous intensity of the normalized surface filtration membrane in the band of re-emission wavelengths of at least one of the fluorescent markers and by comparing said luminous intensity with a calibration curve.

Advantageously, the luminous intensity is measured by integrating the signal from a photovoltaic sensor over a predetermined time interval.

In another embodiment, the luminous intensity is measured in a plurality of different bands of wavelengths corresponding to the re-emission bands of different markers. This embodiment can detect the presence of different cell types.

The invention also concerns an installation for counting cells and micro-organisms and cells of the type comprising a microporous membrane support, a light source for illuminating the membrane and means for analyzing filtrates deposited on the membrane, the analysis means being constituted by at least one photovoltaic sensor adapted to detect the global luminous intensity emitted by a particular surface element of the membrane.

Advantageously, the invention includes a drawer for positioning a microporous membrane, a light source emitting in the range of excitation wavelengths of fluorescent markers disposed on one side of said drawer and at least one sensor having a filter the pass-band of which substantially corresponds to the re-emission band of the fluorescent markers, said sensor and said filter being disposed on the opposite side of the drawer.

The invention can also measure density by transmission or reflection of visible light.

In a first embodiment, the installation includes a CCD sensor adapted to detect the luminous intensity of a microporous membrane surface element.

In a preferred embodiment, the installation includes a plurality of photodiodes adapted to detect the luminous intensity of a microporous membrane surface element.

The photodiodes are advantageously housed in cylindrical bores with a distribution that corresponds to the filtration areas of the microporous membrane, the drawer including indexing means for positioning the membrane relative to said bores.

BRIEF DESCRIPTION OF THE DRAWINGS

The invention will be better understood from a reading of the following description with reference to the accompanying drawings, in which.

DETAILED DESCRIPTION OF THE INVENTION

Figure 1:
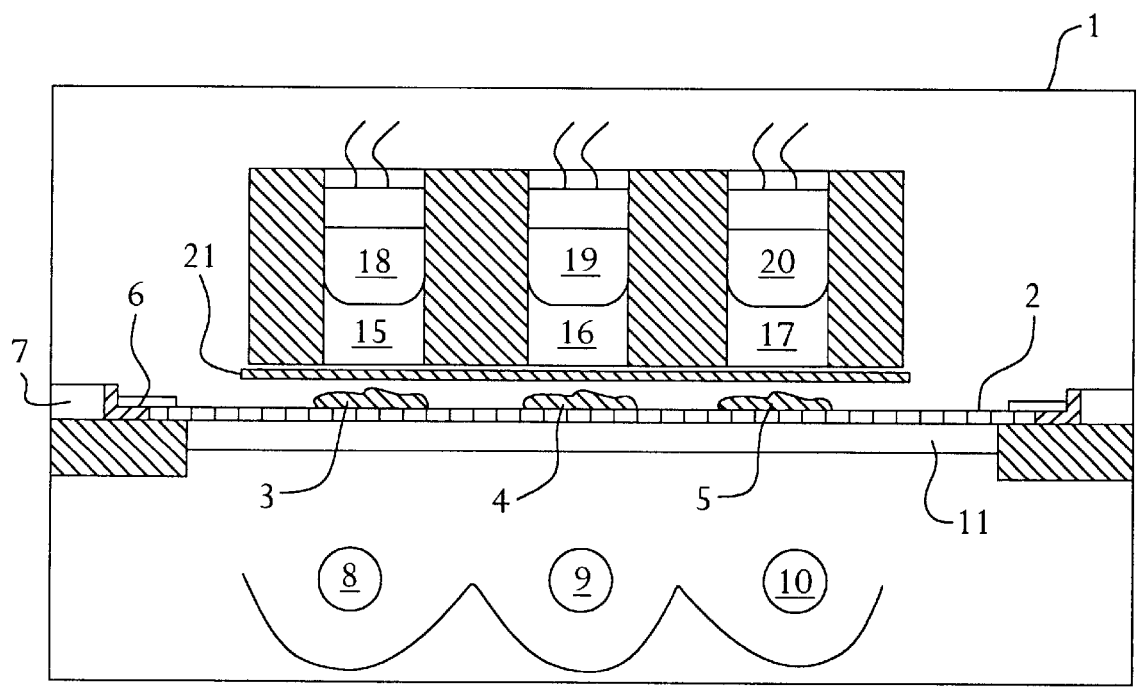
FIG. 1 is a view in section of one embodiment of an installation of the invention.

FIG. 1 is a diagrammatic sectional view of one embodiment of an installation in accordance with the invention for counting cells.

The installation includes a rigid casing (1) with a trapdoor for inserting a microporous membrane (2) in an indexed flexible support carrying filtrates (3–5). The membrane (2) is on a metal support forming a drawer sliding between two guide rails (6, 7).

A row of ultraviolet light sources (8–10) is disposed below the drawer carrying the membrane (2). A band-pass filter (11) passing UV light at the excitation wavelength of the markers is disposed between the row of UV light sources (8–10) and the membrane (2). A metallized reflector (12) reflects some of the light towards the filter (11). On the side opposite the UV light sources the installation includes a set of photodetectors (13) in the form of a unit (14) having a plurality of bores (15, 16, 17) in it directed towards the membrane (2). In each of these cylindrical bores (15–17) is a photodiode (18–20). These photodiodes (18–20) are organized in a matrix with a geometry that corresponds to the geometry of the filter installation which deposits the filtrates (3–5) onto the membrane (2).

A filter (21) is disposed between the membrane (2) and the photodector unit (14). This filter is a band-pass filter passing the wavelengths re-emitted by the fluorescent markers.

Figure 2:
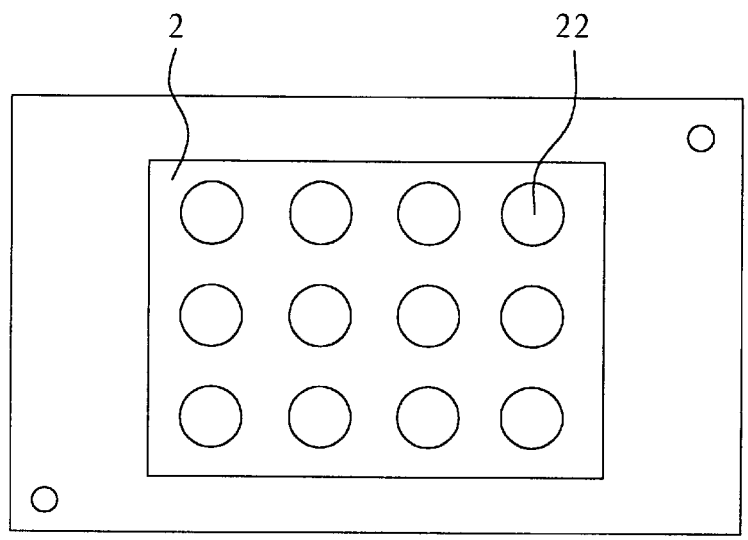
FIG. 2 is a plan view of the microporous membrane placed in its semi-rigid support.

FIG. 2 shows a plan view of one example of a microporous membrane integrated into its COBRA type flexible support ("COBRA" is a registered trademark of the applicant).

The membrane (2) is a matrix of filtration areas (22) the configuration of which is determined by the filtration equipment used and corresponds to the arrangement of the photodiodes.

The operation of the counting installation of the invention is described hereinafter with reference to one example of application concerning the rapid testing of untreated milk.

A sample of untreated milk is taken and if necessary pretreated to digest undesirable constituents such as fat globules and to add a fluorescent coloring agent.

The sample of milk is then filtered using a polycarbonate or polyethylene terephtalate membrane having 2 micron pores on a filter installation such as the "COBRA" equipment sold by BIOCOM. The filter installation enables the simultaneous filtering of several samples and the deposition of a plurality of filtrates onto the membrane in the form of a matrix. The selectivity of the marking process is such that rinsing is not required.

The coloring agent used for marking is ethidium bromide, for example.

After drying in air, the membrane is then placed in a counting installation comprising a 360 nm UV excitation light source and photodiodes associated with a filter passing radiation in the band of wavelengths around 600 nm, for example.

The calibration curve is obtained by comparing the result obtained by the installation of the invention with the result obtained previously, in the laboratory, for example, using prior art methods.

Figure 3:
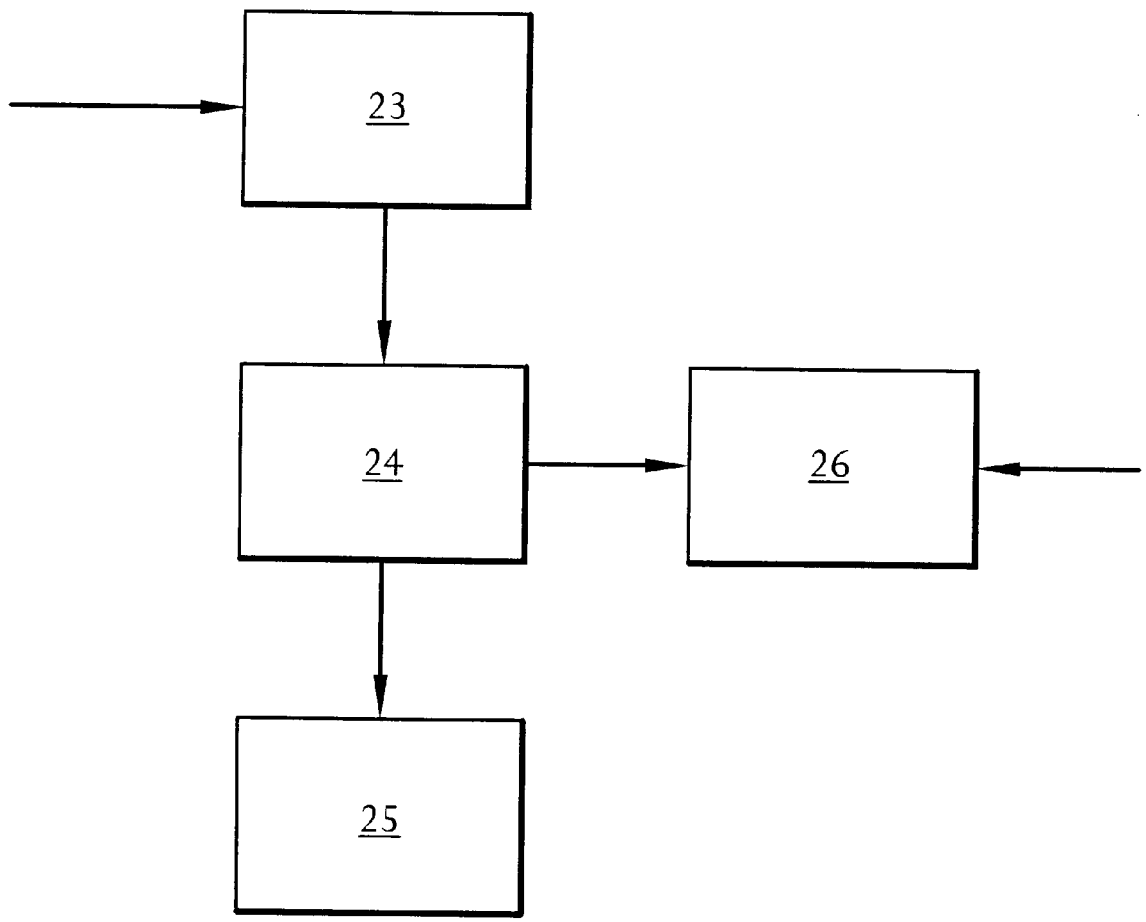
FIG. 3 is a block diagram of the electronic circuits used by the installation.

FIG. 3 shows a block diagram of the electronic circuits used by the installation.

The signal from each photodiode is digitized by a digitizer circuit (23) connected to a microprocessor (24) which processes the signal and calculates the number of cells according to the calibration curve and the luminous intensity measured by the photodiode. The result is shown on a digital display (25) and is recorded in a random access memory (26). This memory contains a file made up of the number of the record, the value of the signal from the photodiode and the number of cells detected.

The memory can also receive the results of counting the same sample using a prior art method. The microprocessor (24) computes a new calibration curve on the basis of this data.

In accordance with the invention, cells or microorganisms are counted according to a protocol for counting the number of cells in milk, one example of which is indicated below:

a 30 µl sample of milk is taken;

this sample is diluted with 1 ml of distilled water;

0.5% formaldehyde is added as a fixing agent together with 5 µg of ethidium bromide per ml of buffer solution (pH=7);

the sample is heated to 60° C. for 20 minutes;

the pretreated sample is filtered using a polycarbonate membrane having a pore size of 2 microns, at a negative pressure of 0.5 bars or a positive pressure of 0.8 bars;

the membrane is placed on the installation of the invention to measure the global luminosity, by excitation using a light source emitting at 360 nm and observation at 580 nm (red region).

One example of a protocol for preparation of samples for counting bacteria in milk consists in:

taking a 100 µl sample of milk;

diluting the sample with 800 µl of a mixture containing:
1.33 mg/ml trypsin,
0.5% triton.

This mixture digests the milk by bursting the somatic cells and the proteins of the milk. The bacteria are not destroyed, as they are protected from digestion by their strong walls.

heating to 47° for 10 minutes;

filtering using a membrane having a pore size of 0.6 µm;

rinsing with a nitrate buffer solution (pH=3);

dyeing with 0.025 acridine (pH=4) for 3 minutes;

rinsing with CITRATE buffer solution (pH=3);

counting with the installation of the invention by excitation using a light source emitting at 260 nm and observation at 580 nm (orange region).

Another example of a protocol for preparation of sample for phenotyping leukemia consists in:

grafting to the surface of the membrane antibodies recognizing particular lymphocytes in a 5 ml sample of blood;

immersion and incubation for 20 minutes, with gentle agitation of the container to encourage adhesion of the lymphocytes;

rinsing the membrane in a buffer solution;

dyeing with ethidium bromide;

reading the various areas to which lymphocytes are fixed to obtain a profile of the population.

Another example of a protocol for preparing samples for phenotyping leukemia consists in:

fixing antibodies to magnetic spherules having a diameter of 1 micron;

incubating for 15 minutes in 1 ml of blood;

introducing a magnet to retain the spherule/cell complex;

eliminating the residues;

filtering the complexes retained by the magnet through a membrane allowing the spherules to pass through freely but not the cells;

dyeing with ethidium bromide;

counting by global measurement in accordance with the invention.

The above description of the present invention is not limiting on the invention. It is evident that the person skilled in the art will be in a position to envisage numerous variants that do not depart from the scope of the invention.

I claim:

1. A method of counting cells and microorganisms present at 50,000 to 1,000,000 cells per milliliter in a fluid medium comprising the steps of: marking the cells and microorganisms in a fluid medium with a fluorescent or colored marker, concentrating the fluid medium by filtering said fluid medium onto a global support having a microporous membrane, simultaneously or prior to counting said cells and microorganisms, measuring the global luminous intensity of the cells and microorganisms on the global support either by transmission or reflection of visible light or by re-emission of light by the fluorescent or colored marker, and comparing the measured global luminous intensity with a calibration curve in order to provide a count of the cells and microorganisms.

2. The method of claim 1 where the fluid medium is selected from the group consisting of food and biological fluids.

3. The method of claim 2 wherein the fluorescent or colored marker is a stoichiometric marker.

4. The method of claim 3 wherein the stoichiometric marker is a DNA marker or an RNA marker.

5. The method of claim 1 wherein the fluorescent or colored marker is a coloring agent selectively marking the cells and microorganisms to be detected and counting of the cells and microorganisms is effected by measuring the global luminous intensity of the global support and comparing said global luminous intensity with a calibration curve.

6. The method of claim 5 wherein the calibration curve is computed by recording data pairs comprising a luminous intensity value of a filtrate and a result of counting the same filtrate by image analysis.

7. The method of claim 1 wherein the fluorescent or colored marker is a fluorescent marker selectively marking the microorganisms and cells to be detected, and said fluorescent marker comprises at least one fluorescent probe, and counting of the cells and microorganisms is effected by measuring the global luminous intensity of the global support in a band of re-emission wavelengths of said at least one fluorescent probe and comparing said global luminous intensity with a calibration curve.

8. The method of claim 7 wherein the fluorescent marker is a DNA marker or an RNA marker with a probe carrying a fluorescent molecule and the steps further comprise simultaneously with or prior to counting the microorganisms and cells, the microorganisms and cells are concentrated by a filtration step using a micro porous filtration membrane that is transparent at an excitation wavelength of the fluorescent marker, and counting of the cells and microorganisms is effected by measuring the global luminous intensity of a normalized surface of the micro porous filtration membrane in a band of re-emission wavelengths of the fluorescent marker and by comparing said global luminous intensity with a calibration curve.

9. The method in claim 8 wherein the global luminous intensity is measured in a plurality of different bands of wavelengths corresponding to the re-emission bands of different fluorescent markers.

10. The method of claim 8 wherein the calibration curve is computed by recording data pairs comprising a luminous intensity value of a filtrate and a result of counting the same filtrate by image analysis.

11. The method in claims 7 wherein the global luminous intensity is measured in a plurality of different bands of wavelengths corresponding to the re-emission bands of different fluorescent markers.

12. The method of claim 7 wherein the calibration curve is computed by recording data pairs comprising a luminous intensity value of a filtrate and a result of counting the same filtrate by image analysis.

13. The method of claim 1 wherein the global luminous intensity is measured by integrating a signal from a photovoltaic sensor over a predetermined time interval.

14. The method in claim 13 wherein the global luminous intensity is measured in a plurality of different bands of wavelengths corresponding to the re-emission bands of different fluorescent markers.

15. Apparatus for counting cells and microorganisms comprising: support means for a concentrated fluid medium containing cells and microorganisms to be analyzed, a light source for illuminating the support means and analysis means wherein, the analysis means are comprised of at least one photovoltaic sensor adapted to detect a global luminous intensity emitted by a particular surface element of the support means.

16. The apparatus of claim 15 further comprising: a support for a micro porous membrane, a light source for illuminating the micro porous membrane, and means for analyzing filtrates deposited on the micro porous membrane wherein the analysis means comprises at least one photovoltaic sensor adapted to detect the global luminous intensity emitted by a particular surface element of the micro porous membrane.

17. The apparatus of claim 16 further comprising: a drawer for positioning said micro porous membrane, a light source which emits a range of excitation wavelengths of fluorescent markers disposed on the under side of said drawer, and at least one sensor having a filter with a pass-band which substantially corresponds to a re-emission band of the fluorescent markers, said at least one sensor having a filter being disposed on the top side of said drawer.

18. The apparatus of claim 17 further comprising a plurality of photo diodes adapted to detect the global luminous intensity of a surface element of the micro porous membrane.

19. The apparatus of claim 18 further comprising: photo diodes housed in cylindrical bores wherein distribution of the cylindrical bores corresponds to filtration areas of the micro porous membrane, and said drawer including indexing means for positioning the micro porous membrane relative to said cylindrical bores.

* * * * *